US007556950B1

United States Patent
Brooun et al.

(10) Patent No.: US 7,556,950 B1
(45) Date of Patent: Jul. 7, 2009

(54) CRYSTALLIZATION OF THE CATALYTIC DOMAIN OF HUMAN PHOSPHODIESTERASE 4-D3 (PDE4-D3)

(75) Inventors: Alexei Brooun, San Diego, CA (US); Ellen Chien, La Jolla, CA (US); Douglas R. Dougan, Calgary (CA); Michelle L. Kraus, Temecula, CA (US); Clifford D. Mol, San Diego, CA (US); Gyorgy Snell, Richmond, CA (US)

(73) Assignee: Takeda San Diego, Inc., San Diego, CA (US)

( * ) Notice: Subject to any disclaimer, the term of this patent is extended or adjusted under 35 U.S.C. 154(b) by 201 days.

(21) Appl. No.: 10/836,040

(22) Filed: Apr. 29, 2004

(51) Int. Cl.
C12N 9/16 (2006.01)
C12N 9/00 (2006.01)
(52) U.S. Cl. .................. 435/196; 435/183; 436/4
(58) Field of Classification Search .................. None
See application file for complete search history.

(56) References Cited

OTHER PUBLICATIONS

Encyclopedia of Molecular Biology (Creighton, T., John Wiley and Sons, Inc. New York, 1999) see pp. 586 and 2725.*
Giege et al., Acta Cryst.-D, vol. 50, pp. 339-350, 1994.*
Kierzek et al., Biophys. Chem., vol. 91, pp. 1-20, 2001.*
Wiencek, Annu. Rev. Biomed. Eng., vol. 1, pp. 505-534, 1999.*
Ke & Doudna, Methods, vol. 34, pp. 408-414, 2004.*
Derewenda et al. Acta Crystallogr. D., vol. 62, pp. 116-124, 2006.*
Buts et al. Acta Crystallogr. D., vol. 61, pp. 1149-1159, 2005.*
Witkowski et al., Biochemistry, vol. 38, pp. 11643-11650, 1999.*
Huai et al. Structure, vol. 11, pp. 865-873, 2003.*
Lee et al. FEBS Letters, vol. 530, pp. 53-58, 2002.*
Baecker et al. Gene, vol. 138, pp. 253-256, 1990.*
Aleshin et al. (1998) FEBS Letters, vol. 434, p. 42-46.*
Branden and Tooze (1999) Introduction to Protein Structure, Garland Publishing, Inc., NY, p. 382.*
Huai et al. (Jul. 2003) Structure, vol. 11, pp. 865-873.*
Bolger et al. (1997) Biochem. J. vol. 328, pp. 539-548.*
MSN encarta Dictionary: lattice, created on Jun. 11, 2007.*
PDB (protein data bank) of 1 OYM and 1Q9M, created Jun. 12, 2007.*
Lee et al. (2002) FEBS Letters, vol. 530, pp. 53-58.*

* cited by examiner

Primary Examiner—David J Steadman
Assistant Examiner—Alexander D Kim
(74) Attorney, Agent, or Firm—David J. Weitz; David Stemerick; Mitchell R. Brustein

(57) ABSTRACT

Provided are crystals relating to human phosphodiesterase 4-D3 (PDE4-D3), methods for forming crystals comprising PDE4-D3 and crystals comprising PDE4-D3 co-crystallized with a ligand molecule, and methods of using crystals comprising PDE4-D3.

9 Claims, 3 Drawing Sheets

Amino acid sequence for full-length human wild type PDE4D3 [SEQ ID NO:1]

(Residues 253-580 are underlined)

```
  1  MMHVNNFPFR RHSWICFDVD NGTSAGRSPL DPMTSPGSGL ILQANFVHSQ RRESFLYRSD
 61  SDYDLSPKSM SRNSSIASDI HGDDLIVTPF AQVLASLRTV RNNFAALTNL QDRAPSKRSP
121  MCNQPSINKA TITEEAYQKL ASETLEELDW CLDQLETLQT RHSVSEMASN KFKRMLNREL
181  THLSEMSRSG NQVSEFISNT FLDKQHEVEI PSPTQKEKEK KKRPMSQISG VKKLMHSSSL
241  TNSSIPRFGV KTEQEDVLAK ELEDVNKWGL HVFRIAELSG NRPLTVIMHT IFQERDLLKT
301  FKIPVDTLIT YLMTLEDHYH ADVAYHNNIH AADVVQSTHV LLSTPALEAV FTDLEILAAI
361  FASAIHDVDH PGVSNQFLIN TNSELALMYN DSSVLENHHL AVGFKLLQEE NCDIFQNLTK
421  KQRQSLRKMV IDIVLATDMS KHMNLLADLK TMVETKKVTS SGVLLLDNYS DRIQVLQNMV
481  HCADLSNPTK PLQLYRQWTD RIMEEFFRQG DRERERGMEI SPMCDKHNAS VEKSQVGFID
541  YIVHPLWETW ADLVHPDAQD ILDTLEDNRE WYQSTIPQSP SPAPDDPEEG RQGQTEKFQF
601  ELTLEEDGES DTEKDSGSQV REDTSCSDSK TLCTQDSEST EIPLDEQVEE EAVGEEEESQ
661  PEACVIDDRS PDT
```

Human cDNA sequence encoding residues 253-580 of PDE4D3 [SEQ ID NO:2]

```
  1  ACTGAACAAG AAGATGTCCT TGCCAAGGAA CTAGAAGATG TGAACAAATG GGGTCTTCAT
 61  GTTTTCAGAA TAGCAGAGTT GTCTGGTAAC CGGCCCTTGA CTGTTATCAT GCACACCATT
121  TTTCAGGAAC GGGATTTATT AAAAACATTT AAAATTCCAG TAGATACTTT AATTACATAT
181  CTTATGACTC TCGAAGACCA TTACCATGCT GATGTGGCCT ATCACAACAA TATCCATGCT
241  GCAGATGTTG TCCAGTCTAC TCATGTGCTA TTATCTACAC CTGCTTTGGA GGCTGTGTTT
301  ACAGATTTGG AGATTCTTGC AGCAATTTTT GCCAGTGCAA TACATGATGT AGATCATCCT
361  GGTGTGTCCA ATCAATTTCT GATCAATACA AACTCTGAAC TTGCCTTGAT GTACAATGAT
421  TCCTCAGTCT TAGAGAACCA TCATTTGGCT GTGGGCTTTA AATTGCTTCA GGAAGAAAAC
481  TGTGACATTT TCCAGAATTT GACCAAAAAA CAAAGACAAT CTTTAAGGAA AATGGTCATT
541  GACATCGTAC TTGCAACAGA TATGTCAAAA CACATGAATC TACTGGCTGA TTTGAAGACT
601  ATGGTTGAAA CTAAGAAAGT GACAAGCTCT GGAGTTCTTC TTCTTGATAA TTATTCCGAT
661  AGGATTCAGG TTCTTCAGAA TATGGTGCAC TGTGCAGATC TGAGCAACCC AACAAAGCCT
721  CTCCAGCTGT ACCGCCAGTG GACGGACCGG ATAATGGAGG AGTTCTTCCC CCAAGGAGAC
781  CGAGAGAGGG AACGTGGCAT GGAGATAAGC CCCATGTGTG ACAAGCACAA TGCTTCCGTG
841  GAAAAATCAC AGGTGGGCTT CATAGACTAT ATTGTTCATC CCCTCTGGGA GACATGGGCA
901  GACCTCGTCC ACCCTGACGC CCAGGATATT TTGGACACTT TGGAGGACAA TCGTGAATGG
961  TACCAGAGCA CAATCCCTCA G
```

FIGURE 1

Amino acid sequence for full-length human wild type PDE4D3 [SEQ ID NO:1]

(Residues 253-580 are underlined)

```
  1    MMHVNNFPFR  RHSWICFDVD  NGTSAGRSPL  DPMTSPGSGL  ILQANFVHSQ  RRESFLYRSD
 61    SDYDLSPKSM  SRNSSIASDI  HGDDLIVTPF  AQVLASLRTV  RNNFAALTNL  QDRAPSKRSP
121    MCNQPSINKA  TITEEAYQKL  ASETLEELDW  CLDQLETLQT  RHSVSEMASN  KFKRMLNREL
181    THLSEMSRSG  NQVSEFISNT  FLDKQHEVEI  PSPTQKEKEK  KKRPMSQISG  VKKLMHSSSL
241    TNSSIPRFGV  KTEQEDVLAK  ELEDVNKWGL  HVFRIAELSG  NRPLTVIMHT  IFQERDLLKT
301    FKIPVDTLIT  YLMTLEDHYH  ADVAYHNNIH  AADVVQSTHV  LLSTPALEAV  FTDLEILAAI
361    FASAIHDVDH  PGVSNQFLIN  TNSELALMYN  DSSVLENHHL  AVGFKLLQEE  NCDIFQNLTK
421    KQRQSLRKMV  IDIVLATDMS  KHMNLLADLK  TMVETKKVTS  SGVLLLDNYS  DRIQVLQNMV
481    HCADLSNPTK  PLQLYRQWTD  RIMEEFFRQG  DRERERGMEI  SPMCDKHNAS  VEKSQVGFID
541    YIVHPLWETW  ADLVHPDAQD  ILDTLEDNRE  WYQSTIPQSP  SPAPDDPEEG  RQGQTEKFQF
601    ELTLEEDGES  DTEKDSGSQV  EEDTSCSDSK  TLCTQDSEST  EIPLDEQVEE  EAVGEEEESQ
661    PEACVIDDRS  PDT
```

Human cDNA sequence encoding residues 253-580 of PDE4D3 [SEQ ID NO:2]

```
  1    ACTGAACAAG  AAGATGTCCT  TGCCAAGGAA  CTAGAAGATG  TGAACAAATG  GGGTCTTCAT
 61    GTTTTCAGAA  TAGCAGAGTT  GTCTGGTAAC  CGGCCCTTGA  CTGTTATCAT  GCACACCATT
121    TTTCAGGAAC  GGGATTTATT  AAAAACATTT  AAAATTCCAG  TAGATACTTT  AATTACATAT
181    CTTATGACTC  TCGAAGACCA  TTACCATGCT  GATGTGGCCT  ATCACAACAA  TATCCATGCT
241    GCAGATGTTG  TCCAGTCTAC  TCATGTGCTA  TTATCTACAC  CTGCTTTGGA  GGCTGTGTTT
301    ACAGATTTGG  AGATTCTTGC  AGCAATTTTT  GCCAGTGCAA  TACATGATGT  AGATCATCCT
361    GGTGTGTCCA  ATCAATTTCT  GATCAATACA  AACTCTGAAC  TTGCCTTGAT  GTACAATGAT
421    TCCTCAGTCT  TAGAGAACCA  TCATTTGGCT  GTGGGCTTTA  AATTGCTTCA  GGAAGAAAAC
481    TGTGACATTT  TCCAGAATTT  GACCAAAAAA  CAAAGACAAT  CTTTAAGGAA  AATGGTCATT
541    GACATCGTAC  TTGCAACAGA  TATGTCAAAA  CACATGAATC  TACTGGCTGA  TTTGAAGACT
601    ATGGTTGAAA  CTAAGAAAGT  GACAAGCTCT  GGAGTTCTTC  TTCTTGATAA  TTATTCCGAT
661    AGGATTCAGG  TTCTTCAGAA  TATGGTGCAC  TGTGCAGATC  TGAGCAACCC  AACAAAGCCT
721    CTCCAGCTGT  ACCGCCAGTG  GACGGACCGG  ATAATGGAGG  AGTTCTTCCC  CAAGGAGAC
781    CGAGAGAGGG  AACGTGGCAT  GGAGATAAGC  CCATGTGTG   ACAAGCACAA  TGCTTCCGTG
841    GAAAAATCAC  AGGTGGGCTT  CATAGACTAT  ATTGTTCATC  CCTCTGGGA   GACATGGGCA
901    GACCTCGTCC  ACCCTGACGC  CCAGGATATT  TTGGACACTT  TGGAGGACAA  TCGTGAATGG
961    TACCAGAGCA  CAATCCCTCA  G
```

FIGURE 1A

Amino acid sequence for residues 253-580 of PDE4D3 with a
N-terminal 6x-histidine tag, spacer region and rTEV cleavage site [SEQ ID NO:3]

(6x-histidine tag, spacer region and rTEV cleavage site are underlined)

```
  1    MSYYHHHHHH DYDIPTTENL YFQGAMDPTE QEDVLAKELE DVNKWGLHVF
 51    RIAELSGNRP LTVIMHTIFQ ERDLLKTFKI PVDTLITYLM TLEDHYHADV
101    AYHNNIHAAD VVQSTHVLLS TPALEAVFTD LEILAAIFAS AIHDVDHPGV
151    SNQFLINTNS ELALMYNDSS VLENHHLAVG FKLLQEENCD IFQNLTKKQR
201    QSLRKMVIDI VLATDMSKHM NLLADLKTMV ETKKVTSSGV LLLDNYSDRI
251    QVLQNMVHCA DLSNPTKPLQ LYRQWTDRIM EEFFRQGDRE RERGMEISPM
301    CDKHNASVEK SQVGFIDYIV HPLWETWADL VHPDAQDILD TLEDNREWYQ
351    STIPQSP
```

CRYSTALLIZATION OF THE CATALYTIC DOMAIN OF HUMAN PHOSPHODIESTERASE 4-D3 (PDE4-D3)

SEQUENCE LISTING

A sequence listing was submitted on two compact discs (CD-ROM/CD-R) in this application, containing a 11 KB size file named "Substitute Sequence Listing (072706) .ST25.txt," created on Jul. 27, 2006, each of which is hereby incorporated reference in its entirety.

FIELD OF THE INVENTION

The present invention relates to a member of a family of phosphodiesterases (PDEs) and more specifically to phosphodiesterase 4-D3 (PDE4-D3). Provided are PDE4-D3 in crystalline form, methods of forming crystals comprising PDE4-D3, and methods of using crystals comprising PDE4-D3.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein. A need thus exists for proteins in crystalline form.

SUMMARY OF THE INVENTION

The present invention is directed to crystals comprising PDE4-D3 and particularly crystals comprising PDE4-D3 that have sufficient size and quality to obtain useful information about the structural properties of PDE4-D3 and molecules or complexes that may associate with PDE4-D3.

In one embodiment, a composition is provided that comprises a protein in crystalline form wherein at least a portion of the protein has 55%, 65%, 75%, 85%, 90%, 95%, 97%, 99% or greater identity with residues 253-580 of SEQ. ID No. 1.

In one variation, the protein has activity characteristic of PDE4-D3. For example, the protein may optionally be inhibited by inhibitors of wild type PDE4-D3. The protein crystal may also diffract X-rays for a determination of structure coordinates to a resolution of 4 Å, 3.5 Å, 3.0 Å, 2.5 Å or less.

In one variation, the protein crystal has a crystal lattice in a $P2_12_12_1$ space group. The protein crystal may also have a crystal lattice having unit cell dimensions, +/−5%, of a=110.48 Å, b=110.47 Å, c=166.20 Å, and $\alpha=\beta=\gamma=90°$.

The present invention is also directed to crystallizing PDE4-D3. The present invention is also directed to the conditions useful for crystallizing PDE4-D3. It should be recognized that a wide variety of crystallization methods can be used in combination with the crystallization conditions to form crystals comprising PDE4-D3 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 253-580 of SEQ. ID No. 1; and storing the crystallization volume under conditions suitable for crystal formation.

In one variation, the crystallization volume comprises the protein in a concentration between 1 mg/ml and 50 mg/ml, and 5-50% w/v of precipitant wherein the precipitant comprises one or more members of the group consisting of PEG having a molecular weight range between 200-20000 and wherein the crystallization volume has a pH between pH 4 and pH 10.

The method may optionally further comprise forming a protein crystal that has a crystal lattice in a $P2_12_12_1$ space group. The method also optionally further comprises forming a protein crystal that has a crystal lattice having unit cell dimensions, +/−5%, of a=110.48 Å, b=110.47 Å, c=166.20 Å, and $\alpha=\beta=\gamma=90°$. The invention also relates to protein crystals formed by these methods.

The present invention is also directed to a composition comprising an isolated protein that comprises or consists of one or more of the protein sequence(s) of PDE4-D3 taught herein for crystallizing PDE4-D3. The present invention is also directed to a composition comprising an isolated nucleic acid molecule that comprises or consists of the nucleotides for expressing the protein sequence of PDE4-D3 taught herein for crystallizing PDE4-D3.

The present invention is also directed to an expression vector that may be used to express the isolated proteins taught herein for crystallizing PDE4-D3. In one variation, the expression vector comprises a promoter that promotes expression of the isolated protein.

The present invention is also directed to a cell line transformed or transfected by an isolated nucleic acid molecule or expression vector of the present invention.

In regard to each of these embodiments, the protein may optionally have activity characteristic of PDE4-D3. For example, the protein may optionally be inhibited by inhibitors of wild type PDE4-D3.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 253-580 of SEQ. ID No. 1; and performing rational drug design using a three dimensional structure that is based on the obtained structure coordinates.

The protein crystals may optionally have a crystal lattice with a $P2_12_12_1$ space group and unit cell dimensions, +/−5%, of a=110.48 Å, b=110.47 Å, and c=166.20 Å, $\alpha=\beta=\gamma=90°$.

The method may optionally further comprise selecting one or more entities based on rational drug design and contacting the selected entities with the protein. The method may also optionally further comprise measuring an activity of the protein when contacted with the one or more entities. The method also may optionally further comprise comparing activity of the protein in the presence of and in the absence of the one or more entities; and selecting entities where activity of the protein changes depending upon whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, and 3 referred to in this application.

DETAILED DESCRIPTION OF THE INVENTION

Figure 2:
FIG. 2 illustrates a crystal of PDE4-D3 corresponding to SEQ. ID No. 3, having a crystal lattice in a $P2_12_12_1$ space group and unit cell dimensions, +/−5%, of a=110.48 Å, b=110.47 Å, c=166.20 Å, and $\alpha=\beta=\gamma=90°$.

The present invention relates to a member of a family of phosphodiesterases and more specifically to a particular PDE known as phosphodiesterase 4-D3 (PDE4-D3). Provided is PDE4-D3 in crystalline form, methods of forming crystals comprising PDE4-D3, and methods of using crystals comprising PDE4-D3.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

It will be readily apparent to those of skill in the art that the numbering of amino acids in other isoforms of PDE4-D3 may be different than that set forth for PDE4-D3 herein. Corresponding amino acids in other isoforms of PDE4-D3 are easily identified by visual inspection of the amino acid sequences or by using commercially available homology software programs, as further described below.

1. PDE4-D3

Phosphodiesterases (PDEs) belong to a large, divergent family which catalyze the hydrolysis of adenosine 3',5'-monophosphate (cAMP) and guanosine 3',5'-monophosphate (cGMP) into the corresponding 5'-nucleotide providing the major pathway for eliminating cyclic nucleotide signals from cells. Changes in intracellular concentration of cAMP and cGMP mediate numerous hormonal and neurotransmitter signals which are important for cell differentiation, growth, survival, and inflammatory processes. Phosphodiesterase 4-D3 (PDE4-D3) is the major cAMP-specific PDE in inflammatory and immune cells making it an excellent target for treating inflammatory and immunological diseases such as asthma and chronic obstructive pulmonary disease.

In many non-infectious human diseases, the extravasal recruitment of neutrophils plays a crucial role in the development of tissue damage, which when persistent may lead to irreversible organ dysfunction. Neutrophil activation is controlled by a number of intracellular pathways, particularly by a cAMP-dependant protein kinase A which also acts on the PDE4 gene stimulating the synthesis of this enzyme to transform cAMP to the inactive AMP. PDE4 inhibitors enhance intracellular cAMP and decrease inflammatory cell activation. Rolipram (Sigma Cat. #R6520), is a well-documented selective inhibitor of the cAMP-specific PDE4.

In one embodiment, PDE4-D3 comprises the wild-type form of full length PDE4-D3, set forth herein as SEQ. ID No. 1 (GenBank Accession Number NM_006203).

In another embodiment, PDE4-D3 comprises residues 253-580 of SEQ. ID No. 1 which comprises the active site domain of wild-type PDE4-D3. The "active site binding pockets" or "active site" of PDE4-D3 refers to the area on the surface of PDE4-D3 where the substrate binds.

It should be recognized that the invention may be readily extended to various variants of wild-type PDE4-D3 and variants of fragments thereof. In another embodiment, PDE4-D3 comprises a sequence wherein at least a portion of the sequence has 55%, 65%, 75%, 85%, 90%, 95%, 97%, 99% or greater identity with SEQ. ID No. 1.

It is also noted that the above sequences of PDE4-D3 are also intended to encompass isoforms, mutants and fusion proteins of these sequences. An example of a fusion protein is provided by SEQ. ID No. 3, which includes a 6 residue N-terminal tag (6 residues are histidine) and a rTev cleavage site that may be used to facilitate purification of the protein.

A wide variety of PDE4-D3 variants (e.g., insertions, deletions, substitutions, etc.) that fall within the above specified identity ranges may be designed and manufactured utilizing recombinant DNA techniques well known to those skilled in the art. These modifications can be used in a number of combinations to produce the variants. The present invention is useful for crystallizing and then solving the structure of the range of variants of PDE4-D3.

Variants of PDE4-D3 may be insertional variants in which one or more amino acid residues are introduced into a predetermined site in the PDE4-D3 sequence. For instance, insertional variants can be fusions of heterologous proteins or polypeptides to the amino or carboxyl terminus of the subunits.

Variants of PDE4-D3 also may be substitutional variants in which at least one residue has been removed and a different residue inserted in its place. Non-natural amino acids (i.e., amino acids not normally found in native proteins), as well as isosteric analogs (amino acid or otherwise), may optionally be employed in substitutional variants. Examples of suitable substitutions are well known in the art, such as Glu→Asp, Asp→Glu, Ser→Cys, and Cys→Ser for example.

Another class of variants is deletional variants, which are characterized by the removal of one or more amino acid residues from the PDE4-D3 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution with bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic acid sequence encoding PDE4-D3 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type PDE4-D3 is functional in the sense that the resulting protein is capable of associating with at least one same chemical entity that is also capable of selectively associating with a protein comprising the wild-type PDE4-D3 (e.g., residues 253-580 of SEQ. ID No. 1) since this common associative ability evidences that at least a portion of the native structure has been conserved.

It is noted that the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of PDE4-D3, and the atomic structure coordinates obtained therefrom, can be used to identify compounds that bind to the native domain. These compounds may affect the activity of the native domain.

Amino acid substitutions, deletions and additions that do not significantly interfere with the three-dimensional structure of PDE4-D3 will depend, in part, on the region where the substitution, addition or deletion occurs in the crystal structure. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; and amino acids with uncharged polar head groups having similar hydrophilicity values include the following: leucine, isoleucine, valine, glycine, alanine, asparagines, glutamine, serine, threonine, phenylalanine, and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of PDE4-D3 will be apparent to those having skills in the art.

2. Cloning, Expression and Purification of PDE4-D3

The gene encoding PDE4-D3 can be isolated from RNA, cDNA or cDNA libraries. In this case, the portion of the gene encoding amino acid residues 253-580 (SEQ. ID No. 1), corresponding to the catalytic domain of PDE4-D3, was isolated and is shown as SEQ. ID No. 2.

Construction of expression vectors and recombinant proteins from the DNA sequence encoding PDE4-D3 may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of PDE4-D3. Example 1 provides one such expression system.

Once expressed, purification steps are employed to produce PDE4-D3 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

PDE4-D3 may optionally be affinity labeled during cloning, preferably with a N-terminal six-histidine tag and rTev cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization and Crystals Comprising PDE4-D3

One aspect of the present invention relates to methods for forming crystals comprising PDE4-D3 as well as crystals comprising PDE4-D3.

In one embodiment, a method for forming crystals comprising PDE4-D3 is provided comprising forming a crystallization volume comprising PDE4-D3, one or more precipitants, optionally a buffer, optionally a monovalent and/or divalent salt and optionally an organic solvent; and storing the crystallization volume under conditions suitable for crystal formation.

In yet another embodiment, a method for forming crystals comprising PDE4-D3 is provided comprising forming a crystallization volume comprising PDE4-D3 in solution comprising the components shown in Table 1; and storing the crystallization volume under conditions suitable for crystal formation.

TABLE 1

Precipitant 5-50% w/v of precipitant wherein the precipitant comprises one or more members of the group consisting of PEG MME having a molecular weight range between 1000-10000, PEG having a molecular weight range between 100-10000, and 0.3-2.0 M Sodium, potassium or ammonium phosphate.

pH pH 4-10. Buffers that may be used include, but are not limited to tris, bicine, phosphate, cacodylate, acetate, citrate, HEPES, PIPES, MES and combinations thereof.

Additives

Optionally 0.05 to 2.5 M additives wherein the additives comprise a monovalent and/or divalent salt (for example, sodium, lithium, magnesium, calcium, and the like)

Protein Concentration 1 mg/ml-50 mg/ml

Temperature

1° C.-25° C.

In yet another embodiment, a method for forming crystals comprising PDE4-D3 is provided comprising forming a crystallization volume comprising PDE4-D3; introducing crystals comprising PDE4-D3 as nucleation sites; and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising PDE4-D3 and crystals comprising PDE4-D3 according to the invention are not intended to be limited to the wild type, full length PDE4-D3 shown in SEQ. ID No. 1 and fragments comprising residues 253-580 of SEQ. ID No. 1. Rather, it should be recognized that the invention may be extended to various other fragments and variants of wild-type PDE4-D3 as described above.

It should also be understood that forming crystals comprising PDE4-D3 and crystals comprising PDE4-D3 according to the invention may be such that PDE4-D3 is optionally complexed with one or more ligands and one or more copies of the same ligand. The ligand used to form the complex may be any ligand capable of binding to PDE4-D3. In one variation, the ligand is a natural substrate. In another variation, the ligand is an inhibitor.

In one particular embodiment, PDE4-D3 crystals have a crystal lattice in the $P2_12_12_1$ space group. PDE4-D3 crystals may also optionally have unit cell dimensions, +/−5%, of a=110.48 Å, b=110.47 Å, c=166.20 Å, and $\alpha=\beta=\gamma=90°$. PDE4-D3 crystals also preferably are capable of diffracting X-rays for determination of atomic coordinates to a resolution of 4 Å, 3.5 Å, 3.0 Å or better.

Crystals comprising PDE4-D3 may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography, 2$^{nd}$ Ed.* (1999), Academic Press Inc. Further descriptions regarding performing crystallization experiments are provided in Stevens et al. (2000) *Curr. Opin. Struct. Biol.:* 10(5):558-63, and U.S. Pat. Nos. 6,296,673; 5,419,278; and 5,096,676.

In one variation, crystals comprising PDE4-D3 are formed by mixing substantially pure PDE4-D3 with an aqueous buffer containing a precipitant at a concentration just below a concentration necessary to precipitate the protein. One suitable precipitant for crystallizing PDE4-D3 is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a PDE4-D3 complex were obtained. In order to accomplish this, systematic broad screen crystallization trials were performed on a PDE4-D3 complex using the sitting drop technique. In each experiment, a 100 nL mixture of PDE4-D3 complex and precipitant was placed on a platform positioned over a well containing 100 µL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect PDE4-D3 crystallization was obtained. Based on this understanding, a series of crystallization conditions were identified that may be used to form crystals comprising PDE4-D3. These conditions are summarized in Table 1. A particular example of crystallization conditions that may be used to form diffraction quality crystals of the PDE4-D3 complex is detailed in Example 2. FIG. 2 illustrates crystals of the PDE4-D3 complex formed using the crystallization conditions provided in Table 1.

One skilled in the art will recognize that the crystallization conditions provided in Table 1 and Example 2 can be varied and still yield protein crystals comprising PDE4-D3. For example, it is noted that variations on the crystallization conditions described herein can be readily determined by taking the conditions provided in Table 1 and performing fine screens around those conditions by varying the type and concentration of the components in order to determine additional suitable conditions for crystallizing PDE4-D3, variants of PDE4-D3, and ligand complexes thereof.

Crystals comprising PDE4-D3 have a wide range of uses. For example, now that crystals comprising PDE4-D3 have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising PDE4-D3 according to the present invention, the crystals so formed can be used by this crystallization technique to initiate crystal growth of other PDE4-D3 comprising crystals, including PDE4-D3 complexed to other ligands.

As will be described herein in greater detail, crystals may also be used to perform X-ray or neutron diffraction analysis in order to determine the three-dimensional structure of PDE4-D3 and, in particular, to assist in the identification of its active site. Knowledge of the binding site region allows rational design and construction of ligands including inhibitors.

Crystallization and structural determination of PDE4-D3 mutants having altered bioactivity allows the evaluation of whether such changes are caused by general structure deformation or by side chain alterations at the substitution site.

4. X-Ray Data Collection and Structure Determination

Crystals comprising PDE4-D3 may be obtained as described above in Section 3. As described herein, these crystals may then be used to perform X-ray data collection and for structure determination.

In one embodiment, described in Example 2, crystals of PDE4-D3 were obtained where PDE4-D3 has the sequence of residues shown in SEQ. ID No. 3. These particular crystals were used to determine the three dimensional structure of PDE4-D3. However, it is noted that other crystals comprising PDE4-D3 including different PDE4-D3 variants, fragments, and complexes thereof may also be used.

Diffraction data were collected from cryocooled crystals (100K) of PDE4-D3 at the Advanced Light Source (ALS) beam line 5.0.3 using an ADSC Quantum CCD detector. The diffraction pattern of the PDE4-D3 crystals displayed symmetry consistent with space group $P2_12_12_1$ with unit cell dimensions a=110.48 Å, b=110.47 Å, c=166.20 Å, and $\alpha=\beta=\beta=90°$ (+/−5%). Data were collected and integrated to 2.5 Å with the HKL2000 program package (Otwinowski, Z. and Minor, W., *Meth. Enzymol.* 276:307 (1997)).

The X-ray diffraction data collection statistics are given in Table 2.

TABLE 2

Crystal data

| | |
|---|---|
| Space group | $P2_12_12_1$ |
| Unit cell dimensions | a = 110.48 Å |

TABLE 2-continued

| | | |
|---|---|---|
| | | b = 110.47 Å |
| | | c = 166.20 Å |
| | | $\alpha = \beta = \gamma = 90°$ |
| Data collection | | |
| X-ray source | | ALS BL 5.0.3 |
| Wavelength [Å] | | 1.00 |
| Resolution [Å] | | 2.50 |
| Observations (unique) | | 68797 |
| Redundancy | | 2.96 |
| Completeness | overall (outer shell) | 96.6 (95.3)% |
| I/σ(I) | overall (outer shell) | 15.7 (2.6) |
| $R_{symm}$[1] | overall (outer shell) | 0.040 (.382) |

Based on crystal volume calculations, where the unit cell dimensions were a=110.48 Å, b=110.47 Å, c=166.20 Å, and $\alpha=\beta=\gamma=90°$, it was realized that the asymmetric unit comprised six PDE4-D3 molecules.

5. Uses of the Crystal and Diffraction Pattern of PDE4-D3

Crystals, crystallization conditions and the diffraction pattern of PDE4-D3 that can be generated from the crystals also have a range of uses. One particular use relates to screening entities that are not known ligands of PDE4-D3 for their ability to bind to PDE4-D3. For example, with the availability of crystallization conditions, crystals and diffraction patterns of PDE4-D3 provided according to the present invention, it is possible to take a crystal of PDE4-D3; expose the crystal to one or more entities that may be a ligand of PDE4-D3; and determine whether a ligand/PDE4-D3 complex is formed. The crystals of PDE4-D3 may be exposed to potential ligands by various methods, including but not limited to, soaking a crystal in a solution of one or more potential ligands or co-crystallizing PDE4-D3 in the presence of one or more potential ligands.

Once one or more ligands are identified, structural information from the ligand/PDE4-D3 complex(es) may be used to design new ligands that bind tighter, bind more specifically, have better biological activity or have better safety profiles than known ligands.

In one embodiment, a method is provided for identifying a ligand that binds to PDE4-D3 comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to PDE4-D3 comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-PDE4-D3 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

According to another embodiment, the invention provides compounds that associate with a PDE4-D3-like binding pocket produced or identified by various methods set forth above. The terms "binding site" or "binding pocket", as used herein, refer to a region of a protein that, as a result of its shape, favorably associates with a ligand or substrate. Similarly, the term "PDE4-D3-like binding pocket" refers to a portion of a molecule or molecular complex whose shape is sufficiently similar to the PDE4-D3 binding pockets as to bind common ligands. This commonality of shape may be quantitatively defined based on a comparison to a reference point (e.g., a set of structure coordinates). For example, the commonality of shape may be quantitatively defined based on a root mean square deviation (RMSD) from the structure coordinates of the backbone atoms of the amino acids that make up the binding pockets in PDE4-D3.

EXAMPLES

Example 1

Expression and Purification of PDE4-D3

This example describes cloning, expression and purification of PDE4-D3. It should be noted that a variety of other expression systems and hosts are also suitable for the expression of PDE4-D3, as would be readily appreciated by one of skill in the art.

The portion of the gene encoding residues 253-580 (from SEQ. ID No. 1), which corresponds to the catalytic domain of human PDE4-D3, was cloned into a modified pFastBacHTc vector (also known as pSXB1) at the BamHI and EcoRI sites. Expression from this vector produced the recombinant PDE4D3 catalytic domain with a 6x-histidine tag at the N-terminus followed by a rTEV protease cleavage sequence to facilitate tag removal (the excised 6x-Histidine tag and rTev cleavage site sequences are underlined in SEQ. ID No. 3). Recombinant baculovirus genomic DNAs incorporating the PDE4D3 catalytic domain cDNA sequences were generated by transposition using the Bac-to-Bac system (Invitrogen). Infectious viral particles were obtained by transfection of a 2 ml adherent culture of *Spodoptera frugiperda* Sf9 insect cells with the recombinant viral genomic DNA. Growth in ESF 921 protein free medium (Expression Systems) was for 3 days at 27° C. The resulting Passage 0 viral supernatant was used to obtain Passage 1 high titer viral stock (HTS) by infection of a 30 ml adherent culture of Spodoptera frugiperda Sf9 insect cells grown under similar conditions. Passage 1 HTS was used in turn to infect a 100 ml suspension culture of *Spodoptera frugiperda* Sf9 insect cells in order to generate Passage 2 HTS.

Passage 2 HTS was used to infect 5-liters of *Trichoplusia ni* Hi5 insect cells (InVitrogen) at a density of approximately $2 \times 10^6$ cells/ml in a 5-liter Wave BioReactor grown in ESF-921 serum-free medium at a multiplicity of infection (moi) of approximately 5 (empirical value based on usual HTS viral counts). Cell growth/infection proceeded for two days after which time the cells were pelleted by centrifugation and the cell pellet stored at −80° C. until required. Frozen cell pellets from two 5-liter cultures were removed from the −80° C. freezer and each suspended in 150 ml of Lysis Buffer (50 mM Tris-HCl, pH 7.9, 200 mM NaCl, 0.25 mM TCEP, 1 mM PMSF and 2 'Complete-EDTA' Roche Protease Inhibitor tablets). The suspensions were stirred for 45 min at 4° C. followed by centrifugation at 5,000 g for 1 h. To each supernatant was added 8 ml of a 50% slurry of ProBond (InVitrogen) resin that had been equilibrated in Lysis Buffer without protease inhibitors. The suspensions were mixed for 90 min followed by centrifugation at 640 g for 5 min. The supernatants were discarded and the resin pellets washed three times with 50 mM potassium phosphate, pH 7.9, 400 mM NaCl, 0.25 mM TCEP and 1 µg/mL leupeptin. Each resin sample was transferred to an OMNI chromatography column (10 cm×1.5 cm diameter) at 4° C. and washed with 50 column volumes of 50 mM potassium phosphate, pH 7.9, 400 mM NaCl, 20 mM imidazole-HCl, pH 7.9, 0.25 mM TCEP and 1 µg/mL leupeptin. The columns were subsequently washed with 5 column volumes of 50 mM Tris-HCl, pH 7.9, 400 mM NaCl, 0.25 mM TCEP and 1 µg/mL leupeptin. Target elution was effected by the addition of 50 mM Tris-HCl, pH 7.9, 400 mM NaCl, 200 mM imidazole-HCl, pH 7.9, 0.25 mM TCEP, 1 µg/mL leupeptin. The eluates were pooled (the yield at this stage was around 80 mg total protein) and the polyhistidine purification tag removed by cleavage overnight with 100 µg/ml TEV protease during dialysis against 50 mM Tris-HCl, pH 7.9, 400 mM NaCl, 20 mM imidazole-HCl, pH 7.9, 0.25 mM TCEP and 1 µg/mL leupeptin at 4° C. The TEV-treated sample was passed by gravity flow through an 8 ml bed volume of ProBond chelating resin charged with Ni that had been equilibrated in 50 mM Tris-HCl, pH 7.9, 400 mM NaCl, 20 mM imidazole-HCl, pH 7.9, 0.25 mM TCEP and 1 µg/mL leupeptin at 4° C. The unbound flow-through material was concentrated and buffer-exchanged into 25 mM Cacodylic buffer, pH 6.5 containing 400 mM NaCl, 5 mM DTT, 1 mM $MgCl_2$, and 2-molar excess of Rolipram (Sigma Cat. #R6520) using Vivaspin centrifugal concentrators. Following two five-fold dilution buffer-exchanges, the purified PDE4-D3 was concentrated to 19.4 mg/ml with a total volume of 2.7 ml (52.4 mg purified PDE4-D3). The purified protein was dimeric by analytical size-exclusion chromatography (SEC) and exhibited a major band by both isoelectric focusing (IEF) and by sodium-dodecyl-sulfate polyacrylamide gel electrophoresis (SDS-PAGE) analyses.

Example 2

Crystallization of PDE4-D3

This example describes the crystallization of PDE4-D3. It is noted that the precise crystallization conditions used may be further varied, for example by performing a fine screen based on these crystallization conditions.

PDE4-D3 protein samples (corresponding to SEQ. ID No. 3) were co-concentrated with Rolipram (Sigma Cat. #R6520)

before setting crystallization trials. Crystals were obtained after an extensive and broad screen of conditions, followed by optimization. Diffraction quality crystals were grown in 100 nl sitting droplets using the vapor diffusion method. 50 nl comprising the PDE4-D3-Rolipram complex (19 mg/ml) was mixed with 50 nL from a reservoir solution (100 μl) comprising: 20% MPEG 5000; 0.1 M HEPES buffer pH=7.2, and 10% isopropanol. The resulting solution was incubated over a period of one week at 4° C. Crystals typically appeared after 2-5 days and grew to a maximum size within 7-10 days. Single crystals were transferred, briefly, into a cryoprotecting solution containing the reservoir solution supplemented with 25% v/v ethylene glycol and 300 mM sodium ascorbate. Crystals were then flash frozen by immersion in liquid nitrogen and then stored under liquid nitrogen. A crystal of the PDE4-D3-Rolipram complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, patent applications, papers, and books cited in this application are incorporated herein in their entirety.

---

We claim:

1. A composition comprising a protein-Rolipram complex in co-crystalline form, wherein the protein of the complex consists of residues 24-357 of SEQ ID NO:3, wherein said protein is in complex with Rolipram, and wherein the co-crystal has a crystal lattice in a P2₁2₁2₁ space group and unit cell dimensions, +/−5%, of a=110.48 Å, b=110.47 Å, c=166.20 Å, and α=β=γ=90°.

2. The composition according to claim 1 wherein the co-crystal diffracts X-rays for a determination of structure coordinates to a resolution having a value of 3.0 Å or less.

3. A method comprising:
    forming a co-crystallization volume comprising a precipitant solution, Rolipram, and a protein consisting of residues 24-357 of SEQ ID NO:3;
    storing the crystallization volume under conditions suitable for co-crystal formation of Rolipram and the protein; and
    forming a protein-Rolipram co-crystal, wherein said protein is in complex with Rolipram, and wherein the protein crystal has a crystal lattice in a P2₁2₁2₁ space group and unit cell dimensions, +/−5%, of a=110.48 Å, b=110.47 Å, c=166.20 Å, and α=β=γ=90°.

4. The method according to claim 3 wherein the protein-Rolipram co-crystal is formed that diffracts X-rays for a determination of structure coordinates to a resolution having a value of 3.0 Å or less.

5. The method according to claim 3 wherein the protein-Roliplram co-crystal is formed that diffracts X-rays for a determination of structure coordinates to a resolution having a value of 2.5 Å or less.

6. A non-crystalline protein consisting of residues 24-357 of SEQ ID NO:3.

7. A non-crystalline protein consisting of SEQ ID NO:3.

8. An isolated non-crystalline protein consisting of residues 24-357 of SEQ ID NO: 3.

9. An isolated non-crystalline protein consisting of SEQ ID NO: 3.

* * * * *

SEQUENCE LISTING

```
<160> NUMBER OF SEQ ID NOS: 3

<210> SEQ ID NO 1
<211> LENGTH: 673
<212> TYPE: PRT
<213> ORGANISM: Homo sapien
<220> FEATURE:
<221> NAME/KEY: MISC_FEATURE
<222> LOCATION: (1)..(673)
<223> OTHER INFORMATION: Amino acid sequence for full length wild type
      PDE4D3

<400> SEQUENCE: 1

Met Met His Val Asn Asn Phe Pro Phe Arg Arg His Ser Trp Ile Cys
1               5                   10                  15

Phe Asp Val Asp Asn Gly Thr Ser Ala Gly Arg Ser Pro Leu Asp Pro
                20                  25                  30

Met Thr Ser Pro Gly Ser Gly Leu Ile Leu Gln Ala Asn Phe Val His
            35                  40                  45

Ser Gln Arg Arg Glu Ser Phe Leu Tyr Arg Ser Asp Ser Asp Tyr Asp
        50                  55                  60

Leu Ser Pro Lys Ser Met Ser Arg Asn Ser Ser Ile Ala Ser Asp Ile
65                  70                  75                  80

His Gly Asp Asp Leu Ile Val Thr Pro Phe Ala Gln Val Leu Ala Ser
                85                  90                  95

Leu Arg Thr Val Arg Asn Asn Phe Ala Ala Leu Thr Asn Leu Gln Asp
                100                 105                 110

Arg Ala Pro Ser Lys Arg Ser Pro Met Cys Asn Gln Pro Ser Ile Asn
            115                 120                 125

Lys Ala Thr Ile Thr Glu Glu Ala Tyr Gln Lys Leu Ala Ser Glu Thr
        130                 135                 140

Leu Glu Glu Leu Asp Trp Cys Leu Asp Gln Leu Glu Thr Leu Gln Thr
145                 150                 155                 160

Arg His Ser Val Ser Glu Met Ala Ser Asn Lys Phe Lys Arg Met Leu
                165                 170                 175

Asn Arg Glu Leu Thr His Leu Ser Glu Met Ser Arg Ser Gly Asn Gln
                180                 185                 190

Val Ser Glu Phe Ile Ser Asn Thr Phe Leu Asp Lys Gln His Glu Val
            195                 200                 205

Glu Ile Pro Ser Pro Thr Gln Lys Glu Lys Glu Lys Lys Lys Arg Pro
        210                 215                 220

Met Ser Gln Ile Ser Gly Val Lys Lys Leu Met His Ser Ser Ser Leu
225                 230                 235                 240
```

-continued

```
Thr Asn Ser Ser Ile Pro Arg Phe Gly Val Lys Thr Glu Gln Glu Asp
                245                 250                 255

Val Leu Ala Lys Glu Leu Glu Asp Val Asn Lys Trp Gly Leu His Val
            260                 265                 270

Phe Arg Ile Ala Glu Leu Ser Gly Asn Arg Pro Leu Thr Val Ile Met
        275                 280                 285

His Thr Ile Phe Gln Glu Arg Asp Leu Leu Lys Thr Phe Lys Ile Pro
    290                 295                 300

Val Asp Thr Leu Ile Thr Tyr Leu Met Thr Leu Glu Asp His Tyr His
305                 310                 315                 320

Ala Asp Val Ala Tyr His Asn Asn Ile His Ala Ala Asp Val Val Gln
                325                 330                 335

Ser Thr His Val Leu Leu Ser Thr Pro Ala Leu Glu Ala Val Phe Thr
            340                 345                 350

Asp Leu Glu Ile Leu Ala Ala Ile Phe Ala Ser Ala Ile His Asp Val
        355                 360                 365

Asp His Pro Gly Val Ser Asn Gln Phe Leu Ile Asn Thr Asn Ser Glu
    370                 375                 380

Leu Ala Leu Met Tyr Asn Asp Ser Ser Val Leu Glu Asn His His Leu
385                 390                 395                 400

Ala Val Gly Phe Lys Leu Leu Gln Glu Glu Asn Cys Asp Ile Phe Gln
                405                 410                 415

Asn Leu Thr Lys Lys Gln Arg Gln Ser Leu Arg Lys Met Val Ile Asp
            420                 425                 430

Ile Val Leu Ala Thr Asp Met Ser Lys His Met Asn Leu Leu Ala Asp
        435                 440                 445

Leu Lys Thr Met Val Glu Thr Lys Lys Val Thr Ser Ser Gly Val Leu
    450                 455                 460

Leu Leu Asp Asn Tyr Ser Asp Arg Ile Gln Val Leu Gln Asn Met Val
465                 470                 475                 480

His Cys Ala Asp Leu Ser Asn Pro Thr Lys Pro Leu Gln Leu Tyr Arg
                485                 490                 495

Gln Trp Thr Asp Arg Ile Met Glu Glu Phe Phe Arg Gln Gly Asp Arg
            500                 505                 510

Glu Arg Glu Arg Gly Met Glu Ile Ser Pro Met Cys Asp Lys His Asn
        515                 520                 525

Ala Ser Val Glu Lys Ser Gln Val Gly Phe Ile Asp Tyr Ile Val His
    530                 535                 540

Pro Leu Trp Glu Thr Trp Ala Asp Leu Val His Pro Asp Ala Gln Asp
545                 550                 555                 560

Ile Leu Asp Thr Leu Glu Asp Asn Arg Glu Trp Tyr Gln Ser Thr Ile
                565                 570                 575

Pro Gln Ser Pro Ser Pro Ala Pro Asp Asp Pro Glu Glu Gly Arg Gln
            580                 585                 590

Gly Gln Thr Glu Lys Phe Gln Phe Glu Leu Thr Leu Glu Glu Asp Gly
        595                 600                 605

Glu Ser Asp Thr Glu Lys Asp Ser Gly Ser Gln Val Glu Glu Asp Thr
    610                 615                 620

Ser Cys Ser Asp Ser Lys Thr Leu Cys Thr Gln Asp Ser Glu Ser Thr
625                 630                 635                 640

Glu Ile Pro Leu Asp Glu Gln Val Glu Glu Ala Val Gly Glu Glu
                645                 650                 655

Glu Glu Ser Gln Pro Glu Ala Cys Val Ile Asp Asp Arg Ser Pro Asp
```

```
                    660           665           670
Thr

<210> SEQ ID NO 2
<211> LENGTH: 981
<212> TYPE: DNA
<213> ORGANISM: Homo sapien
<220> FEATURE:
<221> NAME/KEY: misc_feature
<222> LOCATION: (1)..(981)
<223> OTHER INFORMATION: Human cDNA sequence encoding residues 253-580
      of PDE4D3

<400> SEQUENCE: 2
actgaacaag aagatgtcct tgccaaggaa ctagaagatg tgaacaaatg gggtcttcat      60
gttttcagaa tagcagagtt gtctggtaac cggcccttga ctgttatcat gcacaccatt    120
tttcaggaac gggatttatt aaaaacattt aaaattccag tagatacttt aattacatat    180
cttatgactc tcgaagacca ttaccatgct gatgtggcct atcacaacaa tatccatgct    240
gcagatgttg tccagtctac tcatgtgcta ttatctacac ctgctttgga ggctgtgttt    300
acagatttgg agattcttgc agcaattttt gccagtgcaa tacatgatgt agatcatcct    360
ggtgtgtcca atcaatttct gatcaataca aactctgaac ttgccttgat gtacaatgat    420
tcctcagtct tagagaacca tcatttggct gtgggcttta aattgcttca ggaagaaaac    480
tgtgacattt tccagaattt gaccaaaaaa caaagacaat ctttaaggaa atggtcatt    540 gacatcgtac ttgcaacaga tatgtcaaaa cacatgaatc tactggctga tttgaagact    600
atggttgaaa ctaagaaagt gacaagctct ggagttcttc ttcttgataa ttattccgat    660
aggattcagg ttcttcagaa tatggtgcac tgtgcagatc tgagcaaccc aacaaagcct    720
ctccagctgt accgccagtg gacggaccgg ataatggagg agttcttccc ccaaggagac    780
cgagagaggg aacgtggcat ggagataagc cccatgtgtg acaagcacaa tgcttccgtg    840
gaaaaatcac aggtgggctt catagactat attgttcatc ccctctggga gacatgggca    900
gacctcgtcc accctgacgc ccaggatatt ttggacactt tggaggacaa tcgtgaatgg    960
taccagagca caatccctca g                                              981

<210> SEQ ID NO 3
<211> LENGTH: 357
<212> TYPE: PRT
<213> ORGANISM: Artificial
<220> FEATURE:
<223> OTHER INFORMATION: Amino acid sequence for residues 253-580 of
      PDE4D3 with a N-terminal 6x-histidine tag, spacer region and rTEV
      cleavage site

<400> SEQUENCE: 3

Met Ser Tyr Tyr His His His His His His Asp Tyr Asp Ile Pro Thr
1               5                   10                  15

Thr Glu Asn Leu Tyr Phe Gln Gly Ala Met Asp Pro Thr Glu Gln Glu
            20                  25                  30

Asp Val Leu Ala Lys Glu Leu Glu Asp Val Asn Lys Trp Gly Leu His
        35                  40                  45

Val Phe Arg Ile Ala Glu Leu Ser Gly Asn Arg Pro Leu Thr Val Ile
    50                  55                  60

Met His Thr Ile Phe Gln Glu Arg Asp Leu Leu Lys Thr Phe Lys Ile
65                  70                  75                  80

Pro Val Asp Thr Leu Ile Thr Tyr Leu Met Thr Leu Glu Asp His Tyr
```

-continued

```
                         85                  90                  95
His Ala Asp Val Ala Tyr His Asn Asn Ile His Ala Ala Asp Val Val
                100                 105                 110

Gln Ser Thr His Val Leu Leu Ser Thr Pro Ala Leu Glu Ala Val Phe
                115                 120                 125

Thr Asp Leu Glu Ile Leu Ala Ala Ile Phe Ala Ser Ala Ile His Asp
                130                 135                 140

Val Asp His Pro Gly Val Ser Asn Gln Phe Leu Ile Asn Thr Asn Ser
145                 150                 155                 160

Glu Leu Ala Leu Met Tyr Asn Asp Ser Ser Val Leu Glu Asn His His
                165                 170                 175

Leu Ala Val Gly Phe Lys Leu Leu Gln Glu Glu Asn Cys Asp Ile Phe
                180                 185                 190

Gln Asn Leu Thr Lys Lys Gln Arg Gln Ser Leu Arg Lys Met Val Ile
                195                 200                 205

Asp Ile Val Leu Ala Thr Asp Met Ser Lys His Met Asn Leu Leu Ala
    210                 215                 220

Asp Leu Lys Thr Met Val Glu Thr Lys Lys Val Thr Ser Ser Gly Val
225                 230                 235                 240

Leu Leu Leu Asp Asn Tyr Ser Asp Arg Ile Gln Val Leu Gln Asn Met
                245                 250                 255

Val His Cys Ala Asp Leu Ser Asn Pro Thr Lys Pro Leu Gln Leu Tyr
                260                 265                 270

Arg Gln Trp Thr Asp Arg Ile Met Glu Glu Phe Phe Arg Gln Gly Asp
                275                 280                 285

Arg Glu Arg Glu Arg Gly Met Glu Ile Ser Pro Met Cys Asp Lys His
                290                 295                 300

Asn Ala Ser Val Glu Lys Ser Gln Val Gly Phe Ile Asp Tyr Ile Val
305                 310                 315                 320

His Pro Leu Trp Glu Thr Trp Ala Asp Leu Val His Pro Asp Ala Gln
                325                 330                 335

Asp Ile Leu Asp Thr Leu Glu Asp Asn Arg Glu Trp Tyr Gln Ser Thr
                340                 345                 350

Ile Pro Gln Ser Pro
                355
```